(12) United States Patent
Ollmann et al.

(10) Patent No.: US 6,630,297 B2
(45) Date of Patent: Oct. 7, 2003

(54) METHODS OF SCREENING FOR AGENTS THAT MODULATE THE INTERACTION OF HUMAN ECT2 POLYPEPTIDE WITH AN ECT2 BINDING TARGET

(75) Inventors: Michael Martin Ollmann, Redwood City, CA (US); Kevin Patrick Keegan, San Diego, CA (US); Thomas J. Stout, San Francisco, CA (US); David Matthews, San Francisco, CA (US); Alison Joly, San Mateo, CA (US)

(73) Assignee: Exelixis, Inc., South San Francisco, CA (US)

(\*) Notice: Subject to any disclaimer, the term of this patent is extended or adjusted under 35 U.S.C. 154(b) by 0 days.

(21) Appl. No.: 10/289,779

(22) Filed: Nov. 7, 2002

(65) Prior Publication Data

US 2003/0078382 A1 Apr. 24, 2003

Related U.S. Application Data

(62) Division of application No. 09/976,239, filed on Oct. 12, 2001, now Pat. No. 6,515,109.
(60) Provisional application No. 60/239,689, filed on Oct. 12, 2000.

(51) Int. Cl.$^7$ .............................. C12Q 1/00; C12Q 1/68; G01N 33/53; G01N 33/567; C07K 14/00
(52) U.S. Cl. ................................ 435/4; 435/7.1; 435/6; 435/7.21; 530/350
(58) Field of Search ................................ 435/7.1, 7.21, 435/6, 4; 530/350

(56) References Cited

FOREIGN PATENT DOCUMENTS

WO WO 01/70807 9/2001

OTHER PUBLICATIONS

Tatsumoto et al, Human ECT2 is an exchange factor for Rho GTPases, phosphorylated in G2/M phases, and involved in cytokinesis. J. Cell Biol. 147: 921–927, 1999.\*
Kimura et al, Accumulation of GTP–bound RhoA during cytokinesis and a critical role of ECT2 in this Accumulation. J. Biol. Chem. 275: 17233–17236, 2000.\*
Miki et al, Database Swiss–Prot, Accession No. Q07139, Jul. 15, 1999.8.\*
Miki et al, Oncogene ECT2 is related regulators of small GTP–binding proteins. Nature 362: 462–465, 1993.\*
Lehner, C.F., "The pebble gene is required for cytokinesis in Drosophila", Journal of Cell Science, 1992, 103:1021–1030, The Company of Biologists Limited, Great Britain.
Hegde,P., et al., "EST377993 MAGE resequences, MAGI Homo sapiens cDNA, mRNA sequence" Genbank GI No. 8155756, Jun. 1, 2000.
NCI–CGAP, "tu89e03.x1 NCI_CGAP_Gas4 Homo sapiens cDNA clone IMAGE:2258236 3' similar to TR:Q07139 Q07139 ECT2 ONCOGENE" Genbank GI No. 5636530, Dec. 15, 1999.
NIH–MGC, "UI–HF–BN0–aln–c–10–0–UI.r1 NIH_MGC_50 Homo sapiens cDNA clone IMAGE:3080082 5'" Genbank GI No. 7142453, Mar. 2, 2000.
Dias Neto,E., "QV1–BT0631–150200–071–f05 BT0631 Homo sapiens cDNA, mRNA sequence" Genbank GI No. 8471000, Jun. 12, 2000.
NIH–MGC, "UI–HF–BN0–ala–h–11–0–UI.r1 NIH_MGC_50 Homo sapiens cDNA clone IMAGE:3079149 5'" Genbank GI No. 7142100, Mar. 2, 2000.
Dias Neto,E., "QV1–BT0631–280200–084–d11 BT0631 Homo sapiens cDNA" Genbank GI No. 8471150, Jun. 12, 2000.
Hegde,P., "EST382885 MAGE resequences, MAGKHomo sapiens cDNA" Genbank GI No. 8160647, Jun. 1, 2000.
NCI–CGAP, "zs92g10.r1 NCI_CGAP_GCB1 Homo sapiens cDNA clone IMAGE:704994 5' similar to TR:G293332 G293332 ECT2 PROTEIN.;, mRNA sequence" Genbank GI No. 1921407, Aug. 15, 1997.
Hillier,L., "zq51a07.r1 Stratagene neuroepithelium (#937231) Homo sapiens cDNA clone, IMAGE:645108 5' similar to TR:G293332 G293332 ECT2 PROTEIN" Genbank GI No. 1801929, Jan. 27, 1997.
Adams,M.D., "EST185199 Colon carcinoma (HCC) cell line Homo sapiens cDNA 5' end similar to similar to transforming protein, mRNA sequence" Genbank GI No. 1965630, Apr. 19, 1997.
Miki,T., "Mouse oncogene (ect2) mRNA, complete cds" Genbank GI No. 293331, Jun. 12, 1993.
Miki,T., "ect2" Genbank GI No. 293332, Jun. 12, 1993.
Database EMBL, Accession No. Q948V3, Isogai et al., "NEDO human cDNA sequencing project", Mar. 1, 2001.

\* cited by examiner

Primary Examiner—Elizabeth Kemmerer
Assistant Examiner—Ruixiang Li
(74) Attorney, Agent, or Firm—Laleh Shayesteh; Jan Brunelle

(57) ABSTRACT

Human Ect2 polypeptide, fragments and derivatives, along with vectors and host cells for expression and production of Ect2 polypeptide are provided. Various methods of screening for agents that modulate interaction of Ect2 with an Ect2 binding agent, including high throughput methods, are also provided.

10 Claims, No Drawings

METHODS OF SCREENING FOR AGENTS THAT MODULATE THE INTERACTION OF HUMAN ECT2 POLYPEPTIDE WITH AN ECT2 BINDING TARGET

REFERENCE TO RELATED APPLICATIONS

This application is a divisional application of U.S. patent application Ser. No. 09/976,239, filed Oct. 12, 2001, now U.S. Pat. No. : 6,515,109, which claims priority to U.S. provisional patent application Ser. No. 60/239,689, filed Oct. 12, 2000. The contents of prior applications are hereby incorporated in their entirety.

BACKGROUND OF THE INVENTION

The superfamily of small (21 kDa) GTP binding proteins (small G proteins) comprises 5 subfamilies: Ras, Rho, ADP ribosylation factors (ARFs), Rab, and Ran, which act as molecular switches to regulate numerous cellular responses. Members of the Rho family of GTPases, include RhoA, -B, and -C, Rac1 and -2, and Cdc42. Guanine nucleotide exchange factors (GEFs) activate Rho proteins by catalyzing the replacement of bound GDP with GTP. The GTP-bound form of Rho proteins specifically interact with their effectors or targets and transmit signals to downstream molecules. Rho proteins are inactivated through the hydrolysis of bound GTP to GDP by intrinsic GTPase activity, assisted by GTPase activating proteins (GAPs). The Rho family of GTPases participate in regulation of the actin cytoskeleton and cell adhesion, and are also involved in regulation of smooth muscle contraction, cell morphology, cell motility, neurite retraction, cytokinesis, and cell transformation (Hall, A. Science (1998) 279:509–514).

Ect2, a transforming protein with sequence similarity to the dbl homology (DH) domain proteins, is a GEF that associates with a subset of the Rho family proteins: RhoA, Cdc42, and Rac1. Ect2 phosphorylation, which is required for its exchange activity, occurs during G2 and M phases. Human Ect2 is involved in the regulation of cytokinesis. The human ect2 gene is located on the long arm of chromosome 3, at 3q26 (Takai S, et al., Genomics (1995) 27(1):220–222), a region of increased copy number and expression in a large number of cancers (Bitter M A, et al., Blood (1985) 66(6):1362–1370; Kim D H, et al., Int J Cancer. (1995) 60(6):812–819; Brzoska P M, et al., Cancer Res. (1995) 55(14):3055–3059; Balsara B R, et al., Cancer Res. (1997) 57(11):2116–2120; Heselmeyer K, et al., Genes Chromosomes Cancer (1997) 19(4):233–240; Sonoda G, et al., Genes Chromosomes Cancer. (1997) 20(4):320–8). Data available from the National Cancer Institute (website at ncbi.nlm.nih.gov/ncicgap) indicates that human ect2 is overexpressed in cancers of the ovary, uterus, parathyroid, testis, brain, and colon.

The ect2 gene is conserved at the sequence and functional levels in mammals and insects. The pebble gene in Drosoplila (GenBank ID # (GI) 5817603) is the orthologue of mouse (GI293331) and human ect2, and is required for initiation of cytokinesis (Lehner C F, J. Cell Sci. (1992) 103: 1021–1030; Prokopenko S N, et al., Genes Dev (1999) 13(17):2301–2314).

SUMMARY OF THE INVENTION

The invention provides isolated human Ect2 protein and its splice variant as well as fragments and derivatives thereof. Vectors and host cells expressing Ect2 molecules, as well as methods of production of Ect2 and methods of production of cells for expressing Ect2 are also described.

The invention further provides methods of screening for agents that modulate the interaction of an Ect2 polypeptide with an Ect2 binding target. In one aspect, the screening method comprises the steps of expressing a recombinant Ect2 polypeptide, incubating the polypeptide and the Ect2 binding target with a candidate agent and determining whether the candidate agent modulates the binding of the Ect2 polypeptide with the Ect2 binding target. Preferred modulating agents include Ect2-specific antibodies and small molecules identified in high throughput screens.

The invention further provides novel high throughput assays to measure Ect2 activity.

DETAILED DESCRIPTION OF THE INVENTION

The ability to screen or manipulate the genomes of model organisms provides a powerful means to analyze complex genetic pathways. In particular, overexpression screens in Drosophila enable quick identification of genes involved in the same or overlapping pathways as human genetic pathways (Rorth P., et al., Development (1998) 125:1049–1057; WO0015843). We performed an overexpression screen in Drosophila to identify genes that interact with the cyclin dependent kinase inhibitor, p21 (Boume H R, et al., Nature (1990) 348(6297):125–132; Marshall C J, Trends Genet (1991) 7(3):91–95) Pebble, the Drosophila orthologue of human Ect2, was identified as a suppressor of p21 overexpression. To our knowledge, there are no prior reports in the literature of a link between Ect2 and the G1 phase of the cell cycle, or any evidence that suggests that overexpression of Ect2 can overcome a block in the cell cycle. Our identification of an Ect2 orthologue in the Drosophila p21 screen supports both conclusions. Thus, Ect2 is a valuable "target" that can be used to identify compounds and other agents that modulate its function, and thus have utility in treatment of disease or disorders associated with defective cell cycle progression at G1 phase, and in particular, defective p21 function.

Ect2 Nucleic Acids and Polypeptides

We identified cDNA sequences of human ect2 and a splice variant (SEQ ID NO:1 and SEQ ID NO:3, respectively) through bioinformatic analysis of public databases and "contigging" several incomplete EST sequences (AW965920, AI916675, AW504786, BE080710, AW504433, BE080860, AW970802, AA279942, AA206473, AA313301). Northern Blot analysis of mRNA from tumor samples, using full or partial ect2 cDNA (SEQ ID Nos:1 and 3) sequences as probes (Current Protocol in Molecular Biology, Eds. Asubel, et al., Wiley Interscience, NY), can identify tumors that overexpress Ect2, and that, therefore, are amenable to treatment by inhibition of Ect2 function. Alternatively, quantitative PCR, such as the TaqMan® procedure (PE Applied Biosystems) is used for analysis of Ect2 expression in tumor samples.

The term "Ect2 polypeptide" refers to a full-length Ect2 protein or a fragment or derivative thereof. A preferred Ect2 polypeptide comprises or consists of an amino acid sequence of SEQ ID NO:2 or 4, or a fragment or derivative thereof. Compositions comprising Ect2 polypeptides may consist essentially of the Ect2 protein, fragment, or derivative, or may comprise additional components (e.g. pharmaceutically acceptable carriers or excipients, culture media, etc.).

Ect2 protein derivatives typically share a certain degree of sequence identity or sequence similarity with SEQ ID NOs:2 or 4, or a fragment thereof. As used herein, "percent (%) sequence identity" with respect to a specified subject sequence, or a specified portion thereof, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403–410; website at blast.wustl.edu/blast/README.html) with search parameters set to default values. The HSP S and HSP S2 parameters are dynamic values and are established by the program itself depending upon the composition of the particular sequence and composition of the particular database against which the sequence of interest is being searched. A "% identity value" is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, senne, threonine, cysteine and glycine.

Preferred Ect2 protein derivatives or fragments share at least 80% sequence identity or similarity, preferably at least 85%, more preferably at least 90%, still more preferably at least 95%, and most preferably 97% or 100% sequence identity or similarity with a contiguous stretch of at least 25, 50, 100, 224, or 234 amino acids of SEQ ID NO:2 or 4, and in some cases, the entire length of SEQ ID NO:2 or 4. Preferred derivatives or fragments of Ect2 consist of or comprise an amino acid sequence that has at least 80%, preferably at least 85%, more preferably at least 90%, still more preferably at least 95%, and most preferably 100% sequence identity or sequence similarity with any of amino acid residues 147–227 (BRCT domain), 235–323 (BRCT domain), 327–330 (CDC2 consensus site), 419–617 (RHOGEF domain), 636–765 (PH domain), and 814–817 (CDC2 consensus site) of SEQ ID NO:2, or with any amino acid residues 178–258 (BRCT domain), 266–354 (BRCT domain), 358–361 (CDC2 consensus site), 450–648 (RHOGEF domain), 667–796 (PH domain), and 845–848 (CDC2 consensus site) of SEQ ID NO: 4. Each one of the above domains was identified using the pfam program (Bateman et al., Nucleic Acids Res. (1999) 27:260–262; website at pfam.wustl.edu/), which also contains the detailed description of each domain (BRCT domain: PF00533; RHOGEF domain: PF00621; PH domain: PF00169).

The fragment or derivative of the Ect2 protein is preferably "functionally active" meaning that it exhibits one or more functional activities associated with a full-length, wild-type Ect2 protein comprising the amino acid sequence of SEQ ID NOs:2 or 4. As one example, a fragment or derivative may have antigenicity such that it can be used in immunoassays, for immunization, for modulation of Ect2 activity, etc, as discussed further below regarding generation of antibodies to Ect2 proteins. Preferably, a functionally active Ect2 fragment or derivative is one that displays one or more biological activities associated with Ect2 proteins, such as signaling activity, binding to small GTPases and/or catalysis of GDP/GTP exchange in small GTPases. If Ect2 fragments are used in assays to identify modulating agents, the fragments preferably comprise one or more of the above-mentioned Ect2 domains, or a C- or N-terminus, and preferably comprise at least 10, 20, 25, 50, 224, or 234 contiguous amino acids of SEQ ID NO:1 or 2.

The term "Ect2 nucleic acid" refers to a DNA or RNA molecule that encodes an Ect2 polypeptide. Preferably, the Ect2 polypeptide or nucleic acid or fragment thereof is from a human (e.g. SEQ ID NOs 1–4), but it can be an ortholog or derivative thereof, preferably with at least 70%, 80%, 85%, 90%, or 95% sequence identity with any one of SEQ ID NOs 1–4. Orthologs can be identified by BLAST analysis using SEQ ID NO:2 or 4, using methods known in the art (Huynen M A and Bork P, Proc Natl Acad Sci (1998) 95:5849–5856; Huynen M A et al., Genome Research (2000) 10:1204–1210).

Isolation, Production, and Expression of Ect2 Nucleic Acids and Polypeptides

A wide variety of methods are available for obtaining Ect2 polypeptides. In general, the intended use for the polypeptide will dictate the particulars of expression, production, and purification methods. For instance, production of polypeptides for use in screening for modulating agents may require methods that preserve specific biological activities of these proteins, whereas production of polypeptides for antibody generation may require structural integrity of particular epitopes. Expression of polypeptides to be purified for screening or antibody production may require the addition of specific tags (i.e., generation of fusion proteins). Techniques for the expression, production, and purification of proteins are well known in the art; any suitable means therefor may be used (e.g., Higgins S J and Hames B D (eds.) Protein Expression: A Practical Approach, Oxford University Press Inc., New York 1999; Stanbury P F et al al., Principles of Fermentation Technology, $2^{nd}$ edition, Elsevier Science, New York, 1995; Doonan S (ed.) Protein Purification Protocols, Humana Press, New Jersey, 1996; Coligan J E et al, Current Protocols in Protein Science (eds.), 1999, John Wiley & Sons, New York; U.S. Pat. No. 6,165, 992).

The nucleotide sequence encoding an Ect2 polypeptide can be inserted into any appropriate vector for expression of the inserted protein-coding sequence. The necessary transcriptional and translational signals, including promoter/ enhancer element, can derive from the native ect2 gene and/or its flanking regions or can be heterologous. The ect2 gene may be expressed in prokaryotic or eukaryotic cells. The method of choice depends on the intended use of the protein. In particular, eukaryotic systems are particularly useful when native folding and posttranslational modifications are required. Preferred prokaryotic cells include *Escherichia coli* and *Bacillus subtilis*. Preferred eukaryotic cells include mammalian cells (such as human, mouse, monkey or Chinese hamster ovary cells), yeast cells (such as Pichia and Saccharomyces species) and insect cells (such as Drosophila and various lepidopteran cell lines, e.g. Sf9 cells). Cell extracts or supernatants may be purified in order to isolate the Ect2 polypeptide. Preferred purification techniques include HPLC, size exclusion chromatography, cation and anion exchange chromatography, reverse phase chromatography, affinity chromatography and other protein purification techniques known to those skilled in the art.

The Ect2 polypeptide may be optionally expressed as a fusion or chimeric product, joined via a peptide bond to a heterologous protein sequence. For example, to facilitate detection and/or purification of Ect2 polypeptide, the Ect2 expression vector construct may contain one or more antibody epitope coding sequences introduced at the N-terminus, C-terminus of the Ect2 coding region and/or at any position within the gene sequence. Suitable sequences include the Myc epitope, HA epitope, FLAG epitope or polyhistidine epitope (see, e.g Harlow and Lane (1988) Antibodies, A Laboratory Manual, Cold Spring Harbor Laboratory). As another example, the Ect2 polypeptide may be expressed as a fusion protein joined to a transcriptional reporter such as GFP or luciferase. A chimeric protein can be made by ligating the appropriate nucleic acid sequences encoding the desired amino acid sequences to each other in the proper coding frame using standard methods and expressing the chimeric product. A chimeric protein may also be made by protein synthetic techniques, e.g. by use of a peptide synthesizer (Hunkapiller et al., Nature (1984) 310:105–111).

Structural Analysis of Ect2

Three-dimensional structures of components of the Ect2-G-protein (RhoA/Rac/CDC42) system as studied by single-crystal X-ray crystallography provide insight into the mechanistic details of protein-protein recognition between Ect2 and its target G-protein, the guanine nucleotide exchange activity, and the ability of small-molecule compounds to modulate this activity in a therapeutically beneficial manner.

Various Ect2 polypeptide constructs can be studied by X-ray crystallography such as full-length wild-type human Ect2; full-length human Ect2 with relevant point mutations, as indicated by mechanistic biochemical assays; the sub-construct of the RhoGEF domain of human Ect2 (residues 419–617 of SEQ ID NO:2, or 450–648 of SEQ ID NO:4); constructs of the RhoGEF domain of human Ect2 containing relevant point mutations (enhancing, diminishing, or abrogating GEF activity); the sub-construct of the RhoGEF and PH domains of human Ect2 (residues 419–765 of SEQ ID NO:2, or 450–796 of SEQ ID NO:4); constructs of the RhoGEF and PH domains of human Ect2 containing relevant point mutations (enhancing, diminishing, or abrogating GEF activity); any of the above constructs in their native forms, or with N-terminal tags, or with N-terminal GST fusion proteins; any of the above constructs in phosphorylated or dephosphorylated form; and any of the aforementioned in complex with small-molecule modulators of GEF activity as selected from a compound library.

The crystal structures of these Ect2 polypeptides and complexes are determined through the use of standard techniques (Bergfors, T., Ed., 1999, "Protein Crystallization: Techniques, Strategies, and Tips" International University Line, La Jolla, Calif., USA). Crystallizations are accomplished through the screening of "crystallization space" using standard techniques of "Incomplete Factorial Screening" in a variety of crystallization geometries such as hanging drop, sitting drop, sandwich drop, capillary diffusion, gel equilibration, etc. (McPherson, A., 1989, "Preparation and Analysis of Protein Crystals" R. E. Krieger Publishing Co., Malabar, Fla., USA). Diffraction data are collected from these crystals with the rotation method (Blundell, T. L., Johnson, L. N., 1976, "Protein Crystallography" Academic Press, Harcourt Brace Jovanovich, Publishers; London; Stout & Jensen, 1989, "X-ray Structure Determination, A Practical Guide" John Wiley & Sons, Publishers, New York) both on a rotating anode X-ray generator and at synchrotron sources. Crystal structures are determined by techniques standard in the field, such as molecular replacement (MR), heavy atom phasing via single isomorphous replacement (SIR), heavy atom phasing via single isomorphous replacement with anamolous scattering (SIRAS), heavy atom phasing via multiple isomorphous replacement (MIR), heavy atom phasing via multiple isomorphous replacement with anamolous scattering (MIRAS), and/or heavy atom phasing via isomorphous replacement of methionines with selenomethionine and employing "Multi-wavelength Anamolous Diffraction" (MAD) (Blundell & Johnson; supra; Stout & Jensen, supra; Bella, J.; Rossmann, M. G., 1998, Acta Crystallogr D Biol Crystallogr, 54(Pt 2), 159–74; Fanchon, E.; Hendrickson, W. A., Acta Crystallogr A 1990 Oct 1;46 (Pt 10):809–20; Hendrickson W A; et al., Proteins, 1988 4(2), 77–88; Pahler, A.; et al., 1990, Acta Crystallographica. Section A, Crystal physics, Diffraction, Theoretical and General Crystallography, 46 (Pt 7), 537–40; Terwilliger, T. C., Berendzen, J., 1999, Acta Crystallographica, Section D, Biological Crystallography, 55(Pt 4), 849–61; and Walsh, M. A., et al., 1999 Acta Crystallogr D Biol Crystallogr, 55(Pt 10), 1726–32).

Functional Validation

In general, functional assays are used to confirm the participation of the Ect2 gene and its orthologs in p21-related pathways. Various preferred assays for functional validation of Ect2 in the p21 pathway include expression analysis, and cell transformation, proliferation, cell cycle, apoptosis, and hypoxia induction assays, among others.

A preferred functional validation assay for Ect2 is expression analysis. Several methods are available to assess whether altered Ect2 expression is correlated with tumorogenicity, or another p21-related phenotype. These include Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112–125; Kallioniemi OP, Ann Med 2001, 33:142–147; BloMP21 DH and Guiseppi-Elie, A Curr Opin Biotechnol 2001, 12:41–47). In one example, Northern blot analysis of mRNA from tumor and normal cell lines, and from tumor and matching normal tissue samples from the same patients, using full or partial Ect2 cDNA sequences as probes, can determine whether particular tumors overexpress Ect2. Alternatively, the TaqMan® is used for quantitative RT-PCR analysis of Ect2 expression in cell lines, normal tissues and tumor samples (PE Applied Biosystems).

Apoptosis, cell proliferation, cell cycle, cell transformation, and hypoxia induction assays typically involve comparing these cellular events in wild type cells and cells with altered expression of an Ect2 protein. These assays may use tumor or other cells or cell lines with increased or decreased expression of an Ect2 protein, such as those identified by expression analysis, as described above. Alternatively, the assays may use cells engineered to specifically overexpress an Ect2 protein, using above-described expression methods. The assay may also use cells specifically engineered to disrupt expression of an Ect2 protein, such as by RNA inhibition (Elbashir S M et al. Nature 2001, 411: 494–498) or using antisense oligomers, as further described below.

Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al., 1994, Nature 371, 346), by following the incorporation of fluorescein-dUTP (Yonehara et al., 1989, J. Exp. Med. 169, 1747). Apoptosis may further be assayed by acridine orange staining of tissue culture cells (Lucas, R., et al., 1998, Blood 15:4730–41).

Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al., 1988, J. Immunol. Meth. 107, 79). Cell Proliferation may also be examined using [$^3$H]-thymidine incorporation (Chen, J., 1996, Oncogene 13:1395–403; Jeoung, J., 1995, J. Biol. Chem. 270:18367–73). This assay allows for quantitative characterization of S-phase DNA syntheses. In this assay, cells synthesizing DNA will incorporate [$^3$H]-thymidine into newly synthesized DNA. Incorporation can then be measured by standard techniques such as by counting of radioisotope in a scintillation counter (e.g., Beckman LS 3800 Liquid Scintillation Counter). Cell proliferation may also be assayed by colony formation in soft agar (Sambrook et al., Molecular Cloning, Cold Spring Harbor (1989)). Cells transformed with Ect2 are seeded in soft agar plates, and colonies are measured and counted after two weeks incubation.

Angiogenesis may be assayed using various human endothelial cell systems, such as umbilical vein, coronary artery, or dermal cells. The assays might include Alamar Blue based assays (available from Biosource International) to measure proliferation; migration assays using fluorescent molecules, such as the use of Becton Dickinson Falcon HTS FluoroBlock cell culture inserts to measure migration of cells through membranes in presence or absence of angiogenesis enhancer or suppressors; or tubule formation assays based on the formation of tubular structures by endothelial cells on Matrigel™ (Becton Dickinson).

Involvement of a gene in the cell cycle may be assayed by flow cytometry. Cells transfected with an Ect2 may be stained with propidium iodide and evaluated in a flow cytometer (available from Becton Dickinson).

Induction by hypoxic conditions may be assayed by growing cells transfected with MP21 in hypoxic conditions (such as with 0.1% $O_2$, 5% $CO_2$, and balance $N_2$, generated in a Napco 7001 incubator (Precision Scientific)) and normoxic conditions, followed by assessment of gene activity or expression by Taqman®.

Production of Genetically Modified Animals

The methods of this invention may use non-human animals that have been genetically modified to alter expression of Ect2 and/or other genes known to be involved in regulation of the G1 phase of the cell cycle, such as p21. Preferred genetically modified animals are mammals. Preferred non-mammalian species include Zebrafish, C. elegans, and Drosophila. Preferably, the altered Ect2 or other gene expression results in a detectable phenotype, such as increased or reduced cell proliferation relative to control animals having normal expression of the altered gene. The genetically modified animals can be used to further elucidate the p21 pathway, in animal models of pathologies associated with cell proliferation disorders, and for in vivo testing of candidate therapeutic agents, as described below.

Preferred genetically modified animals are transgenic, at least a portion of their cells harboring non-native nucleic acid that is present either as a stable genomic insertion or as an extra-chromosomal element, which is typically mosaic. Preferred transgenic animals have germ-line insertions that are stably transmitted to all cells of progeny animals.

Non-native nucleic acid is introduced into host animals by any expedient method. Methods of making transgenic non-human animals are well-known in the art (for mice see Brinster et al., Proc. Nat. Acad. Sci. USA 1985, 82:4438–42; U.S. Pat. Nos. 4,736,866, 4,870,009, 4,873,191, 6,127,598; Hogan, B., Manipulating the Mouse Embryo, Cold Spring Harbor Laboratory Press, Cold Spring Harbor, N.Y., (1986); for homologous recombination see Capecchi, Science1989, 244:1288–1292; Joyner et al., Nature1989, 338:153–156; for particle bombardment see U.S. Pat. No. , 4,945,050; for Drosophila see Rubin and Spradling, Science (1982) 218:348–53, U.S. Pat. No. 4,670,388; for transgenic insects see Berghammer A. J. et al., Nature 1999, 402:370–371; for Zebrafish see Lin S. Methods Mol Biol. (2000) ;136:375–3830; for fish, amphibians and birds see Houdebine and Chourrout, Experientia (1991) 47:897–905; for rats see Hammer et al., Cell (1990)63:1099–1112; for embryonic stem (ES) cells see Teratocarcinomas and Embryonic Stem Cells, A Practical Approach, E. J. Robertson, ed., IRL Press (1987); for livestock see Pursel et al., Science (1989) 244:1281–1288; for nonhuman animal clones see Wilmut, I. et al. (1997) Nature 385:810–813, PCT Publication Nos. WO 97/07668 and WO 97/07669; for recombinase systems for regulated transgene expression see, Lakso et al., PNAS (1992) 89:6232–6236; U.S. Pat. No. 4,959,317 [for cre.loxP] and O'Gorman et al., Science (1991) 251:1351–1355; U.S. Pat. No. 5,654,182 [for FLP/FRT).

Homozygous or heterozygous alterations in the genomes of transgenic animals may result in mis-expression of native genes, including ectopic expression, over-expression (e.g. by multiple gene copies), under-expression, and non-expression (e.g. by gene knock-out or blocking expression that would otherwise normally occur). In one application, a "knock-out" animal is generated, typically using homologous recombination, in which an alteration in an endogenous gene causes a decrease in that gene's function, preferably such that gene expression is undetectable or insignificant.

Ect2-Modulating Agents

The invention provides methods to identify agents that interact with and/or modulate the function of Ect2 and/or the p21 pathway. Such agents are useful in a variety of diagnostic and therapeutic applications associated with diseases or disorders involving a defective p21 pathway, as well as in further analysis of the Ect2 protein and its contribution to the p21 pathway. Accordingly, the invention also provides methods for modulating the p21 pathway comprising the step of specifically modulating Ect2 activity by administering Ect2-interacting or -modulating agent.

In a preferred embodiment, Ect2-modulating agents inhibit or enhance Ect2 activity or otherwise affect normal Ect2 function, including transcription, protein expression, protein localization, and cellular or extra-cellular activity. In a further preferred embodiment, the candidate p21 pathway-modulating agent specifically modulates the function of the Ect2. The phrases "specific modulating agent", "specifically modulates", etc., are used herein to refer to modulating agents that directly bind to the Ect2 polypeptide or nucleic acid, and preferably inhibit, enhance, or otherwise alter the function of the Ect2. The term also encompasses modulating agents that alter the interaction the Ect2 with a binding partner or substrate (e.g. by binding to a binding partner of an Ect2, or to a protein/binding partner complex, and inhibiting function).

Preferred Ect2-modulating agents include small molecule chemical agents, Ect2-interacting proteins, including antibodies and other biotherapeutics, and nucleic acid modulators, including antisense oligomers and RNA. The modulating agents may be formulated in pharmaceutical compositions, for example, as compositions that may comprise other active ingredients, as in combination therapy, and/or suitable carriers or excipients. Methods of formulating biotherapeutic agenst are described in detail in U.S. Pat. No. 6,146,628. Techniques for formulation and administration of compounds may be found in "Remington's Pharmaceutical Sciences" Mack Publishing Co., Easton, Pa., $19^{th}$ edition.

Small Molecule Modulators

Small molecule modulators are typically organic, non-peptide molecules, having a molecular weight less than 10,000, preferably less than 5,000, more preferably less than 1,000, and most preferably less than 500. This class of modulators includes chemically synthesized molecules, for instance, compounds from combinatorial chemical libraries. Small molecule modulators may be rationally designed based on known structural properties, for example, discerned using method described above. Structures of Ect2 in complex with the partner G-protein (RhoA/Rac/CDC42) show the details of protein-protein interactions required for the GEF activity and can be used to aid in the rational design of small-molecule compounds that modulate the mechanics of these interactions, thereby disrupting the GEF functionality. Structures of Ect2 polypeptides in complex with small-molecule ligands which serve to modulate the GEF activity delineate the portions of the Ect2 molecule which are either directly involved in the catalytic active site or which exert an allosteric effect on the active site, thereby modulating the GEF activity. These modulators of Ect2/GEF activity bind within a radius of 25 Å, 20 Å, 15 Å, 10 Å, 5 Å, or 1.8 Å of certain residues, such as serine 571 ( . . . RLPSVA . . . ), thereby defining a productive binding mode that modulates GEF activity. Small molecule modulators may also be identified by screening compound libraries.

Alternative small molecule modulators include natural products, particularly secondary metabolites from organisms such as plants or fungi, which can also be identified by screening compound libraries for Ect2-modulating activity. Methods for generating and obtaining compounds are well known in the art (Schreiber S L, Science (2000) 151: 1964–1969; Radmann J and Gunther J, Science (2000) 151:1947–1948).

Small molecule modulators identified from screening assays, as described below, can be used as lead compounds from which candidate clinical compounds may be designed, optimized, and synthesized. Such clinical compounds may have utility in treating pathologies associated with the defective p21 signaling. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

An Ect2-interacting protein may be endogenous, i.e. one that normally interacts genetically or biochemically with an Ect2, such as a member of the p21 pathway that modulates Ect2 expression, localization, and/or activity. Ect2-modulators include dominant negative forms of Ect2-interacting proteins and of Ect2 proteins themselves. Yeast two-hybrid and variant screens offer preferred methods for identifying endogenous Ect2-interacting (Finley, R. L. et al. (1996) in DNA Cloning-Expression Systems: A Practical Approach, eds. Glover D. & Hames B. D (Oxford University Press, Oxford, England), pp. 169–203; Fashema SF et al., Gene (2000) 250:1–14; Drees BL Curr Opin Chem Biol (1999) 3:64–70; Vidal M and Legrain P Nucleic Acids Res (1999) 27:919–29; and U.S. Pat. No. 5,928,868). Mass spectrometry offers alternative preferred methods for the elucidation of protein complexes (reviewed in, e.g., Pandley A and Mann M, Nature (2000) 405:837–846; Yates J R $3^{rd}$, Trends Genet (2000) 16:5–8).

An Ect2-interacting protein may be exogenous protein, such as an Ect2-specific antibody or a T-cell antigen receptor (see, e.g., Harlow and Lane (1988) Antibodies, A Laboratory Manual, Cold Spring Harbor Laboratory). Ect2 antibodies are further discussed below.

In one preferred embodiment, an Ect2-interacting protein specifically binds an Ect2 protein. In an alternative preferred embodiment an Ect2-modulating agent binds an Ect2 substrate, binding partner, or cofactor. In certain applications when Ect2-interacting proteins are used in screens to identify small molecule modulators, the binding specificity of the interacting protein to the Ect2 protein may be assayed by various known methods, including binding equilibrium constants (usually at least about $10^7$ $M^{-1}$, preferably at least about $10^8$ $M^{-1}$, more preferably at least about $10^9$ $M^{-1}$), and immunogenic properties. For enzymes and receptors, binding may be assayed by, respectively, substrate and ligand processing.

Specific Antibodies

In a preferred embodiment, the Ect2-interacting protein is an antibody. Antibodies that specifically bind Ect2 polypeptides can be generated using known methods. Preferably the antibody is specific to a mammalian Ect2 polypeptide, and more preferably, a human Ect2. Antibodies may be polyclonal, monoclonal (mAbs), humanized or chimeric antibodies, single chain antibodies, Fab fragments, F(ab') .sub.2 fragments, fragments produced by a FAb expression library, anti-idiotypic (anti-Id) antibodies, and epitope-binding fragments of any of the above. Monoclonal antibodies with affinities of $10^8$ $M^{-1}$ preferably $10^9$ $M^{-1}$ to $10^{10}$ $M^{-1}$, or stronger can be made by standard procedures as described (Harlow and Lane, Antibodies: A Laboratory Manual, CSH Laboratory (1988); Goding (1986) Monoclonal Antibodies: Principles and Practice (2d ed) Academic Press, New York; and U.S. Pat. Nos. 4,381,292; 4,451,570; and 4,618,577). Antibodies may be generated against extracts of cells that express Ect2 or from substantially purified Ect2 or fragments thereof. If Ect2 fragments are used, they preferably comprise at least 10, and more preferably, at least 20 contiguous amino acids of an Ect2 protein. In a particular embodiment Ect2-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of Ect2-specific antibodies is assayed by an appropriate assay such as a solid phase enzyme-linked immunosorbant assay (ELISA) using immobilized corresponding Ect2 polypeptides. Other assays, such as radioimmunoassays or fluorescent assays might also be used.

Chimeric antibodies specific to Ect2 polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851–6855; Neuberger et al., Nature (1984) 312:604–608; Takeda et al., Nature (1985) 31:452–454). Humanized antibodies, which are a form of chimeric antibodies, can be generated by grafting complementary-determining regions (CDRs) (Carlos, T. M., J. M. Harlan., Blood (1994) 84:2068–2101) of mouse antibodies into a background of human framework regions and constant regions by recombinant DNA technology (Riechmann L M, et al., Nature (1988) 323:323–327). Humanized antibodies contain ~10% murine sequences and ~90% human sequences, and thus further reduce or eliminate immunogenicity, while retaining the antibody specificities (Co MS, and Queen C., Nature (1991) 351:501–501; Morrison S L., Ann. Rev. Immun. (1992) 10:239–265). Humanized antibodies and methods of their production are well-known in the art (U.S. Pat Nos. 5,530,101; 5,585,089; 5,693,762, and 6,180,370).

Ect2-specific single chain antibodies, which are recombinant, single chain polypeptides formed by linking the heavy and light chain fragments of the Fv regions via an amino acid bridge, can be produced (U.S. Pat. No. 4,946,778; Bird, Science (1988) 242:423–426; Huston et al., Proe. Natl. Acad. Sci. USA (1988) 85:5879–5883; and Ward et al., Nature (1989) 334:544–546).

Other suitable techniques for antibody production involve in vitro exposure of lymphocytes to the antigenic polypeptides or alternatively to selection of libraries of antibodies in phage or similar vectors (Huse et al., Science (1989) 246:1275–1281).

The polypeptides and antibodies of the present invention may be used with or without modification. Frequently, the polypeptides and antibodies will be labeled by joining, either covalently or non-covalently, a substance that provides for a detectable signal, or that is toxic to cells that express the targeted protein (Menard S, et al., Int J. Biol Markers (1989) 4:131–134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816,567). Antibodies to cytoplasmic proteins may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg–to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Nonaqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies' concentrations in such vehicles are typically in the range of about 1 mg/ml–to about 10 mg/ml. Immunotherapeutic methods are further described in the literature (U.S. Pat. No. 5,859,206; WO0073469).

Nucleic Acid Modulators

Other preferred Ect2-modulating agents comprise nucleic acid molecules, such as antisense oligomers or double stranded RNA (dsRNA), which generally inhibit Ect2 activity.

Preferred antisense oligomers interfere with the function of Ect2 nucleic acids, such as DNA replication, transcription, Ect2 RNA translocation, translation of protein from the Ect2 RNA, RNA splicing, and any catalytic activity in which the Ect2 RNA participates. In one embodiment, the antisense oligomer is an oligonucleotide that is sufficiently complementary to an Ect2 mRNA to bind to and prevent translation from the Ect2 mRNA, preferably by binding to the 5' untranslated region. Ect2-specific antisense oligonucleotides preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA, a chimeric mixture of DNA and RNA, derivatives or modified versions thereof, single-stranded or double-stranded. The oligonucleotide can be modified at the base moiety, sugar moiety, or phosphate backbone. The oligonucleotide may include other appending groups such as peptides, agents that facilitate transport across the cell membrane, hybridization-triggered cleavage agents, and intercalating agents.

In another embodiment, the antisense oligomer is a phosphorothioate morpholino oligomer (PMO). PMOs are assembled from four different morpholino subunits, each of which containing one of four genetic bases (A, C, G, or T) linked to a six-membered morpholine ring. Polymers of these subunits are joined by non-ionic phosphodiamidate inter-subunit linkages. Methods of producing and using PMOs and other antisense oligonucleotides are well known in the art (e.g. see WO99/18193; Summerton J, and Weller D, Antisense Nucleic Acid Drug Dev 1997, 7:187–95; Probst J C, Methods (2000) 22:271–281; U.S. Pat Nos. 5,325,033 and 5,378,841).

Antisense oligomers are commonly used as research reagents, diagnostics, and therapeutics. For example, antisense oligonucleotides, which are able to specifically inhibit gene expression, are often used to elucidate the function of particular genes (see, e.g., U.S. Pat. No. 6,165,790). Antisense oligomers are also used, for example, to distinguish between functions of various members of a biological pathway. Antisense oligomers have been employed as therapeutic moieties in the treatment of disease states in animals and humans and have been demonstrated in numerous clinical trials to be safe and effective (Milligan J F, et al, Current Concepts in Antisense Drug Design, J Med Chem. (1993) 36:1923–1937; Tonkinson J L et al., Antisense Oligodeoxynucleotides as Clinical Therapeutic Agents, Cancer Invest. (1996) 14:54–65). Accordingly, in one aspect of the invention, an Ect2-specific antisense oligomer is used in an assay to further elucidate the function of Ect2 in the p21 pathway. In another aspect of the invention, an Ect2-specific antisense oligomer is used as a therapeutic agent for treatment of metabolic pathologies.

Alternative preferred Ect2-modulating agents are double-stranded RNA species mediating RNA interference (RNAi). RNAi is the process of sequence-specific, posttranscriptional gene silencing in animals and plants, initiated by double-stranded RNA (dsRNA) that is homologous in sequence to the silenced gene. Methods relating to the use of RNAi to silence genes in *C. elegans,* Drosophila, plants, and mammals are known in the art (Fire A, et al., 1998 Nature 391:806–811; Fire, A. Trends Genet. 15, 358–363 (1999); Sharp, P. A. RNA interference 2001. Genes Dev. 15, 485–490 (2001); Hammond, S. M., et al., Nature Rev. Genet. 2, 110–1119 (2001); Tuschl, T. Chem. Biochem. 2, 239–245 (2001); Hamilton, A. et al., Science 286, 950–952 (1999); Hammond, S. M., et al., Nature 404, 293–296 (2000); Zamore, P. D., et al., Cell 101, 25–33 (2000); Bernstein, E., et al., Nature 409, 363–366 (2001); Elbashir, S. M., et al., Genes Dev. 15, 188–200 (2001); WO0129058; WO9932619, and Elbashir S M, et al., 2001 Nature 411:494–498).

Assay Systems

The invention provides assay systems for identifying specific modulators of Ect2 activity. In general, primary assays are used to identify or confirm a modulator's specific biochemical or molecular effect with respect to the Ect2 nucleic acid or protein. In general, secondary assays further assess the activity of an Ect2-modulating agent identified by a primary assay and may confirm that the modulating agent affects Ect2 in a manner relevant to the p21 pathway and cell cycle regulation.

Primary Assays

The type of modulator tested generally determines the type of primary assay.

For small molecule modulators, screening assays are used to identify candidate modulators. Screening assays may be cell-based or may use a cell-free system that recreates or retains the relevant biochemical reaction of the target protein (reviewed in Sittampalam G S et al., Curr Opin Chem Biol (1997) 1:384–91 and accompanying references). As used herein the term "cell-based" refers to assays using live cells, dead cells, or a particular cellular fraction, such as a membrane, endoplasmic reticulum, or mitochondrial fraction. Cell-based screening assays usually require systems for recombinant expression of Ect2 and any auxiliary proteins demanded by the particular assay. The term "cell free" encompasses assays using substantially purified protein (either endogenous or recombinantly produced), partially purified cellular extracts, or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second messengers, immunogenicty and changes in cellular morphology or other cellular characteristics. Appropriate screening assays may use a wide range of detection methods including fluorescent (Klebe C, et al., Biochemistry (1995) 34:12543–12552), radioactive (Hart M, et al., Nature (1991) 354:311–314), colorimetric, spectrophotometric, and amperometric methods, to provide a read-out for the particular molecular event detected, often in high throughput screening (HTS) formats (for example, see Hertzberg R P, and Pope A J, Current Opinion in Chemical Biology (2000) 4:445–451).

Assays for binding agents include screens for compounds that modulate Ect2 interaction with a natural Ect2 binding target. The Ect2 polypeptide used in such assays may be fused to another polypeptide such as a peptide tag for detection or anchoring, etc. In a particular embodiment, the binding target is RhoA, RhoC, Rac, or Cdc42, or portion thereof that provides binding affinity and avidity to the subject Ect2 polypeptide conveniently measurable in the assay and preferably comparable to the intact RhoA, RhoC, Rac, or Cdc42. The Ect2 and binding target are incubated in the presence and absence (i.e. control) of a candidate Ect2 modulating agent under conditions whereby, but for the presence of the candidate modulating agent, the Ect2 polypeptide specifically binds the cellular binding target, portion or analog with a reference binding affinity. After incubation, the agent-biased binding between the Ect2 polypeptide and one or more binding targets is detected by any of a variety of methods depending on the nature of the product and other assay components, such as through optical or electron density, radiative emissions, nonradiative energy transfers, etc. or indirect detection with antibody conjugates, etc. A difference in the binding affinity of Ect2 to the target in the absence of the agent, as compared with the binding affinity in the presence of the agent indicates that the agent modulates the binding of the Ect2 to the Ect2 binding target. A difference, as used herein, is statistically significant and preferably represents at least a 50%, preferably at least 60%, more preferably 75%, and most preferably a 90% difference.

We developed a solid-phase radiometric high throughput assay format to measure activity of Ect2, and other GEFs. The GTPase/GEF activity is evaluated by measuring the binding of the activating ligand -GTP in solid phase. In this assay, the GTPase (such as Rho or Rac) is adsorbed to the bottom of commercially available plates, such as Flashplate (Perkin Elmer Life Sciences), which have scintillant coated on the bottom and sides of the wells. The plates are then washed to remove excess protein. A test compound (candidate modulating agent) is added, followed by GEF (such as ect2, or a functional Ect2 fragment such as a fragment comprising the Dbl homology domain), followed by 35S labeled GTP. When the radioisotope is associated with the solid phase it is measured in a scintillation counter just as if liquid scintillant had been added. Thus, following incubation, the plates are simply counted without further processing, since only 35S-GTP that is exchanged onto the GTPase will be detected. Unbound radioactive GTP remains in solution and is undetectable. Magnesium chloride is used as a negative control. In the absence of GEF, 2 mM $MgCl_2$ prevents GTP from binding, and thus, reduces the number of cpm/well. Inclusion of GEF in the assay will rescue the $MgCl_2$ inhibited exchange.

Other preferred assay formats use fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:730–4; Fernandes P B, Curr Opin Chem Biol (1998) 2:597–603; Hertzberg R P and Pope A J, Curr Opin Chem Biol (2000) 4:445–451). We developed an FMAT (Fluorescent Microvolume Assay Technology) assay format to measure the protein-protein interaction of a GEF and GTPase, whereby GST-fused GTPase (such as RhoA, RhoC, or Rac) is attached to polystyrene beads and the GEF (such as Ect2) is labeled with Cy5 (a long wavelength fluorophore, available from Amersham). When the GTPase and the GEF are associated, there is an increase in fluorescence associated with GTPase beads, which settle to the bottom of the well and are detected using an FMAT 8100 HTS system (Applied Biosystems). Potential inhibitors interfere with the GEF-GTPase association with subsequent decrease in fluorescence.

For antibody modulators, appropriate primary assays test the antibody's specificity for and affinity to the Ect2 protein.

Methods for testing antibody specificity and affinity are well known in the art. Alternatively or additionally, primary assays for antibody modulators may comprise the screening assays described above, used to detect the Ect2 modulator's specific activity.

For nucleic acid modulators, primary assays may test the ability of the nucleic acid modulator to inhibit Ect2 mRNA or protein expression. In general, expression analysis comprises comparing Ect2 expression in like populations of cells (e.g., two pools of cells that endogenously or recombinantly express Ect2) in the presence and absence of the nucleic acid modulator. Methods for analyzing mRNA and protein expression are well known in the art. For instance, Northern blotting, slot blotting, ribonuclease protection, quantitative RT-PCR (e.g., using the TaqMan®, PE Applied Biosystems), or microarray analysis may be used to confirm that Ect2 MRNA expression is reduced in cells treated with the nucleic acid modulator (e.g., Current Protocols in Molecular Biology (1994) Ausubel F M et al., eds., John Wiley & Sons, Inc., chapter 4; Freeman W M et al., Biotechniques (1999) 26:112–125; Kallioniemi O P, Ann Med 2001, 33:142–147; Blohm D H and Guiseppi-Elie, ACurr Opin Biotechnol 2001, 12:41–47). Proteins are most commonly detected with specific antibodies or antisera directed against either the Ect2 protein or specific peptides. Protein expression can be monitored using by a variety of means including Western blotting, the enzyme-linked immunosorbent assay (ELISA), or in situ detection (Harlow E and Lane D (eds.) Using Antibodies: A Laboratory Manual, 1999, Cold Spring Harbor Laboratory Press, New York).

Secondary Assays

Secondary validation can use essentially the same assays used to functionally validate the participation of an ect2 gene in a p21 related pathway. Whereas the afore-described functional validation assays generally compare cells expressing altered levels of an Ect2 protein, secondary validation assays generally compare like populations of cells (e.g., two pools of wild type cells) in the presence and absence of the candidate modulator.

In another embodiment, secondary validation may use the same assays used for high throughput screening. These methods can confirm the activity of a modulator not identified through high throughput screening, such as an antibody or an antisense oligonucleotide modulator, or can confirm the activity of a small molecule modulator identified using a different high throughput screening assay. These assays may also be used to confirm the specificity of a candidate modulator.

Additionally, the modulator is assayed for its effectiveness on the Ect2 in a p21 related manner. Such assays include cell cycle, apoptosis, proliferation, and hypoxic induction assays, among others, as described above. To assess the role of modulators, these assays are performed in presence or absence of the modulator in p21 normal and p21 mutated backgrounds. These assays may use cell lines deficient in p21 such as HCT116 colon cancer cells, among others, available from ATCC (American Type Culture Collection, Manassas, Va.).

Therapeutic and Diagnostic Applications

When used for anti-tumor therapy in a patient, Ect2 modulating agents are administered to the patient in therapeutically effective amounts that eliminate or reduce the patient's tumor burden. They will normally be administered parenterally, when possible at the target cell site, or intravenously. The dose and dosage regimen will depend upon the nature of the cancer (primary or metastatic), its population, the target site, the characteristics of the particular immunotoxin (when used), e.g., its therapeutic index, whether the agent is administered in combination with other therapeutic agents, and the patient's history. The amount of agent administered will typically be in the range of approximately 0.1–10 mg/kg of patient weight.

For parenteral administration, the agents will be formulated in a unit dosage injectable or inhalable (solution, suspension, emulsion) form in association with a pharmaceutically acceptable vehicle, typically in a concentration of about 1–10 mg/ml.

Antibodies that specifically bind Ect2 may be used for the diagnosis of conditions or diseases characterized by expression of Ect2, or in assays to monitor patients being treated with Ect2 modulating agents. Diagnostic assays for Ect2 include methods which utilize the antibody and a label to detect Ect2 in human body fluids or extracts of cells or tissues. The antibodies may be used with or without modification, and may be labeled by joining them, either covalently or non-covalently, with a reporter molecule.

Diagnosis of conditions characterized by expression of Ect2 may also be accomplished by any of a variety of methods such as Northern or TaqMan® analysis (discussed supra) to measure expression of Ect2 in patient samples.

The following experimental section and examples are offered by way of illustration and not by way of limitation.

EXAMPLES

I. High Throughput Fluorescent or Radioactive Homogeneous Assay

Various combinations of fluorescently (with N-Methylanthraniloyl, Bodipy or other commonly used fluorophores) or radioactively (3H, 35S, or 33P) labeled GTP, GDP, dGTP, or dGTP and ect2 are added to each well of a 96-well plate, along with a test compound of choice. Fluorescent measurements (of over 500 nm to reduce background fluorescence) or radioactivity measurements indicative of the exchange reaction are then taken.

The above assay may be performed where all components are in solution, or alternatively, where at least one component is attached to beads that are 10 nm or larger in diameter (such as SPA beads from Amersham, Alpha screen beads from Packard, or FMAT beads from PE Biosystems).

II. High Throughput Elisa Format Assay

Various combinations of Glutathione-S-transferase/ RhoA, Rhoc, RAC, or CDC42 polypeptide fusion protein and biotinylated Ect2 are added to each well of a microtiter plate (Reacti-Bind Streptavidin-Coated, White Polystyrene Plates (#15118B), which have been blocked by Super-Blocking Reagent from Pierce) in assay buffer (0.01M HEPES, 0.15M NaCl, 0.002M $MgCl_2$). Test compounds are then added to each well, and incubated at room temperature for 1 hour. Anti-GST, rabbit and anti-rabbit antibodies are then added to each well and incubated on ice for 1 hour. Plates are then washed with water, diluted Supersignal substrate is added to each well, and chemiluminescence is then measured.

III. Solid Phase Rac1-dbl Screen

3×30 plates/day

Day 1

Reconstitute 4×10 mg GST-Rac1 in 4×10 ml Assay Buffer
Prepare 3 L Assay Buffer (to 1 L 1.4 mM Tris pH7.5, 5 mM
    $MgCl_2$, 0.3% sucrose, 0.1% dextran add 1 ml 1M DTT/L)

Dilute GST-Rac1 into 100 ml Assay Buffer
Mix
Dilute into 1 L Assay Buffer
Mix
Dilute into 2 L Assay Buffer.
Giving a final volume of 2 L of 10 ug/ml GST-Rac1 in Assay Buffer.
Coat 90 Flashplates (Perkin Elmer Life Sciences) with 0.5 ug/well GST-Rac1
(50 ul of 10 ug/ml GST-cdc42 in Assay Buffer)
Place at 4° C. overnight
Prepare 2 L TBS (50 mM Tris-HCl, pH 7.4, 150 mM NaCl).
Day 2.
Thaw 1 vial (1 mCi) [$^{35}$S]GTPγS.
Wash 30 GST-cdc42 coated plates 3×70 ul TBS
Dilute compound in plates by addition of 10 ul Assay Buffer
Transfer 5 ul compound dilution to assay plates
Prepare 0.1 L of Assay buffer containing 1 mCi [$^{35}$S]GTPγS, 500 nM Dbl
Add 5 ul/well dbl/GTPγS (columns 1&2 receive buffer alone)
Seal
Incubate @ room temp×1 hour
Count in the Trilux Scintillation counter
Prepare the remaining 2×30 plates as described above and store at room temp.

IV. FMAT GEF Assay 0.5 ml Protein G polystyrene beads (7 u, 0.5% w/v Spherotech [Libertyville, Ill.]) are washed three times with PBS and resuspended in 0.5 ml PBS. For monitoring of biomolecular binding events, Anti-GST (0.25 ug BIAcore [Uppsala, Sweden]) is added and incubated at room temperature for 30 minutes. The beads are then washed three times with PBS and resuspended in 0.5 ml PBS. The sample is split into 2×0.25 ml aliquots and 2.5 ug of either GST or GST-RhoA is added and incubated at room temperature for 30 minutes. The beads are then washed three times with PBS and resuspended in 0.25 ml PBS.

(His)6 tagged Ect2-dbl domain is labeled with Cy 5 using a Cy5 monoclonal antibody labeling kit according to the manufacturers instruction (Amersham).

To 400 ul of PBS add 4 ul of either "RhoA-beads" or "GST-beads" giving a final concentration of 20 nM RhoA or GST. Add 200 nM Cy5-Ect2_dbl. Mix and aliquot 8×50 ul into a 96 well FMAT plate. Incubate at room temperature for 1 hour and read in the Cy5 detecting channel of an FMAT 8100 HTS system.

All references cited herein, including sequence information in referenced Genbank identifier numbers and website references, are incorporated herein in their entireties.

What is claimed is:

1. A method of screening for agents that modulate the interaction of an ECT2 polypeptide having guanine nucleotide exchange factor activity and comprising the amino acid sequence consisting of SEQ ID NO: 4 with an ECT2 binding target, comprising incubating said ECT2 polypeptide and said binding target with a candidate agent under conditions conducive for binding and determining whether said candidate agent modulates the binding of the ECT2 polypeptide with the ECT2 binding target.

2. The method of claim 1, wherein said binding target is a natural intracellular substrate, and said modulation of the binding of the ECT2 polypeptide with the ECT2 binding target is detected as GDP/GTP exchange of said substrate.

3. The method of claim 1, wherein binding of ECT2 polypeptide and binding target in presence of said candidate agent is detected in solid phase.

4. The method of claim 1 wherein said binding target is selected from the group consisting of RhoA, RhoC, Rac, CDC42.

5. The method of claim 1 wherein said agent is an antibody.

6. The method of claim 1 wherein said agent is a small organic molecule.

7. The method of claim 1 wherein said agent is an antisense oligomer.

8. The method of claim 1 further comprising assaying an agent that modulates the binding of the ECT2 polypeptide with the ECT2 binding target in a secondary assay selected from the group consisting of cell cycle assay, apoptosis assay, proliferation assay, and hypoxic induction assay.

9. The method of claim 8 wherein the secondary assay is a cell-based assay.

10. The method of claim 9 wherein the cell based assay comprises a cell line deficient in p21.

* * * * *

SEQUENCE LISTING

<160> NUMBER OF SEQ ID NOS: 4

<210> SEQ ID NO 1
<211> LENGTH: 2652
<212> TYPE: DNA
<213> ORGANISM: Homo sapiens

<400> SEQUENCE: 1

```
atggctgaaa atagtgtatt aacatccact actgggagga ctagcttggc agactcttcc      60 attttgatt ctaaagttac tgagatttcc aaggaaaact tacttattgg atctacttca     120
tatgtagaag aagagatgcc tcagattgaa acaagagtga tattggttca agaagctgga     180
aaacaagaag aacttataaa agccttaaag gacattaaag tgggctttgt aaagatggag     240
tcagtggaag aatttgaagg tttggattct ccggaatttg aaaatgtatt tgtagtcacg     300
gactttcagg attctgtctt taatgacctc tacaaggctg attgtagagt tattggacca     360
ccagttgtat taaattgttc acaaaaagga gagcctttgc cattttcatg tcgcccgttg     420
tattgtacaa gtatgatgaa tctagtacta tgctttactg gatttaggaa aaaagaagaa     480
ctagtcaggt tggtgacatt ggtccatcac atgggtggag ttattcgaaa agactttaat     540
tcaaaagtta cacatttggt ggcaaattgt acacaaggag aaaaattcag ggttgctgtg     600
agtctaggta ctccaattat gaagccagaa tggatttata agcttggga aaggcggaat     660 gaacaggatt tctatgcagc agttgatgac tttagaaatg aatttaaagt tcctccattt     720
caagattgta ttttaagttt cctgggatt tcagatgaag agaaaaccaa tatggaagaa     780
atgactgaaa tgcaaggagg taaatattta ccgcttggag atgaaagatg cactcacctt     840
gtagttgaag agaatatagt aaaagatctt ccctttgaac cttcaaagaa actttatgtt     900
gtcaagcaag agtggttctg gggaagcatt caaatggatg cccgagctgg agaaactatg     960
tatttatatg aaaaggcaaa tactcctgag ctcaagaaat cagtgtcaat gctttctcta    1020
```

-continued

```
aatacccta acagcaatcg caaacgacgt cgtttaaaag aaacacttgc tcagctttca    1080
agagagacag acgtgtcacc atttccaccc cgtaagcgcc catcagctga gcactccctt    1140
tccatagggt cactcctaga tatctccaac acaccagagt ctagcattaa ctatggagac    1200
accccaaagt cttgtactaa gtcttctaaa agctccactc cagttccttc aaagcagtca    1260
gcaaggtggc aagttgcaaa agagctttat caaactgaaa gtaattatgt taatatattg    1320
gcaacaatta ttcagttatt tcaagtacca ttggaagagg aaggacaacg tggtggacct    1380
atccttgcac cagaggagat taagactatt tttggtagca tcccagatat ctttgatgta    1440
cacactaaga taaaggatga tcttgaagac cttatagtta attgggatga gagcaaaagc    1500
attggtgaca ttttcctgaa atattcaaaa gatttggtaa aaacctaccc tccctttgta    1560
aacttctttg aaatgagcaa ggaaacaatt attaaatgtg aaaaacagaa accaagattt    1620
catgcttttc tcaagataaa ccaagcaaaa ccagaatgtg gacggcagag ccttgttgaa    1680
cttcttatcc gaccagtaca gaggttaccc agtgttgcat tactttttaaa tgatcttaag    1740 aagcatacag ctgatgaaaa tccagacaaa agcactttag aaaaagctat tggatcactg    1800
aaggaagtaa tgacgcatat taatgaggat aagagaaaaa cagaagctca aaagcaaatt    1860
tttgatgttg tttatgaagt agatggatgc cagctaatc ttttatcttc tcaccgaagc    1920
ttagtacagc gggttgaaac aatttctcta ggtgagcacc cctgtgacag aggagaacaa    1980
gtaactctct tcctcttcaa tgattgccta gagatagcaa gaaaacggca caaggttatt    2040 ggcacttta ggagtcctca tggccaaacc cgaccccag cttctcttaa gcatattcac    2100
ctaatgcctc tttctcagat taagaaggta ttggacataa gagagacaga agattgccat    2160
aatgcttttg ccttgcttgt gaggccacca acagagcagg caaatgtgct actcagtttc    2220
cagatgacat cagatgaact tccaaaagaa actggctaa agatgctgtg tcgacatgta    2280
gctaacacca tttgtaaagc agatgctgag aatcttatt atactgctga tccagaatcc    2340
tttgaagtaa atacaaaaga tatgacagt acattgagta gagcatcaag agcaataaaa    2400
aagacttcaa aaaaggttac aagagcattc tctttctcca aaactccaaa aagagctctt    2460
cgaagggctc ttatgacatc ccacggctca gtggagggaa gaagtccttc cagcaatgat    2520
aagcatgtaa tgagtcgtct ttctagcaca tcatcattag caggtatccc ttctccctcc    2580
cttgtcagcc ttccttcctt cttttgaaagg agaagtcata cgttaagtag atctacaact    2640
catttgatat ga                                                        2652
```

<210> SEQ ID NO 2
<211> LENGTH: 883
<212> TYPE: PRT
<213> ORGANISM: Homo sapiens

<400> SEQUENCE: 2

Met Ala Glu Asn Ser Val Leu Thr Ser Thr Gly Arg Thr Ser Leu
1               5                   10                  15

Ala Asp Ser Ser Ile Phe Asp Ser Lys Val Thr Glu Ile Ser Lys Glu
            20                  25                  30

Asn Leu Leu Ile Gly Ser Thr Ser Tyr Val Glu Glu Met Pro Gln
        35                  40                  45

Ile Glu Thr Arg Val Ile Leu Val Gln Glu Ala Gly Lys Gln Glu Glu
    50                  55                  60

Leu Ile Lys Ala Leu Lys Asp Ile Lys Val Gly Phe Val Lys Met Glu
65                  70                  75                  80

```
Ser Val Glu Glu Phe Glu Gly Leu Asp Ser Pro Glu Phe Glu Asn Val
                85                  90                  95
Phe Val Val Thr Asp Phe Gln Asp Ser Val Phe Asn Asp Leu Tyr Lys
            100                 105                 110
Ala Asp Cys Arg Val Ile Gly Pro Val Val Leu Asn Cys Ser Gln
        115                 120                 125
Lys Gly Glu Pro Leu Pro Phe Ser Cys Arg Pro Leu Tyr Cys Thr Ser
        130                 135                 140
Met Met Asn Leu Val Leu Cys Phe Thr Gly Phe Arg Lys Lys Glu Glu
145                 150                 155                 160
Leu Val Arg Leu Val Thr Leu Val His His Met Gly Gly Val Ile Arg
            165                 170                 175
Lys Asp Phe Asn Ser Lys Val Thr His Leu Val Ala Asn Cys Thr Gln
        180                 185                 190
Gly Glu Lys Phe Arg Val Ala Val Ser Leu Gly Thr Pro Ile Met Lys
        195                 200                 205
Pro Glu Trp Ile Tyr Lys Ala Trp Glu Arg Arg Asn Glu Gln Asp Phe
        210                 215                 220
Tyr Ala Ala Val Asp Asp Phe Arg Asn Glu Phe Lys Val Pro Pro Phe
225                 230                 235                 240
Gln Asp Cys Ile Leu Ser Phe Leu Gly Phe Ser Asp Glu Glu Lys Thr
            245                 250                 255
Asn Met Glu Glu Met Thr Glu Met Gln Gly Gly Lys Tyr Leu Pro Leu
            260                 265                 270
Gly Asp Glu Arg Cys Thr His Leu Val Val Glu Glu Asn Ile Val Lys
        275                 280                 285
Asp Leu Pro Phe Glu Pro Ser Lys Lys Leu Tyr Val Val Lys Gln Glu
        290                 295                 300
Trp Phe Trp Gly Ser Ile Gln Met Asp Ala Arg Ala Gly Glu Thr Met
305                 310                 315                 320
Tyr Leu Tyr Glu Lys Ala Asn Thr Pro Glu Leu Lys Lys Ser Val Ser
            325                 330                 335
Met Leu Ser Leu Asn Thr Pro Asn Ser Asn Arg Lys Arg Arg Arg Leu
            340                 345                 350
Lys Glu Thr Leu Ala Gln Leu Ser Arg Glu Thr Asp Val Ser Pro Phe
        355                 360                 365
Pro Pro Arg Lys Arg Pro Ser Ala Glu His Ser Leu Ser Ile Gly Ser
        370                 375                 380
Leu Leu Asp Ile Ser Asn Thr Pro Glu Ser Ser Ile Asn Tyr Gly Asp
385                 390                 395                 400
Thr Pro Lys Ser Cys Thr Lys Ser Ser Lys Ser Ser Thr Pro Val Pro
            405                 410                 415
Ser Lys Gln Ser Ala Arg Trp Gln Val Ala Lys Glu Leu Tyr Gln Thr
        420                 425                 430
Glu Ser Asn Tyr Val Asn Ile Leu Ala Thr Ile Ile Gln Leu Phe Gln
        435                 440                 445
Val Pro Leu Glu Glu Glu Gly Gln Arg Gly Gly Pro Ile Leu Ala Pro
        450                 455                 460
Glu Glu Ile Lys Thr Ile Phe Gly Ser Ile Pro Asp Ile Phe Asp Val
465                 470                 475                 480
His Thr Lys Ile Lys Asp Asp Leu Glu Asp Leu Ile Val Asn Trp Asp
            485                 490                 495
```

```
Glu Ser Lys Ser Ile Gly Asp Ile Phe Leu Lys Tyr Ser Lys Asp Leu
            500                 505                 510

Val Lys Thr Tyr Pro Pro Phe Val Asn Phe Glu Met Ser Lys Glu
            515                 520                 525

Thr Ile Ile Lys Cys Glu Lys Gln Lys Pro Arg Phe His Ala Phe Leu
            530                 535                 540

Lys Ile Asn Gln Ala Lys Pro Glu Cys Gly Arg Gln Ser Leu Val Glu
545                 550                 555                 560

Leu Leu Ile Arg Pro Val Gln Arg Leu Pro Ser Val Ala Leu Leu Leu
            565                 570                 575

Asn Asp Leu Lys Lys His Thr Ala Asp Glu Asn Pro Asp Lys Ser Thr
            580                 585                 590

Leu Glu Lys Ala Ile Gly Ser Leu Lys Glu Val Met Thr His Ile Asn
            595                 600                 605

Glu Asp Lys Arg Lys Thr Glu Ala Gln Lys Gln Ile Phe Asp Val Val
            610                 615                 620

Tyr Glu Val Asp Gly Cys Pro Ala Asn Leu Leu Ser Ser His Arg Ser
625                 630                 635                 640

Leu Val Gln Arg Val Glu Thr Ile Ser Leu Gly Glu His Pro Cys Asp
                645                 650                 655

Arg Gly Glu Gln Val Thr Leu Phe Leu Phe Asn Asp Cys Leu Glu Ile
                660                 665                 670

Ala Arg Lys Arg His Lys Val Ile Gly Thr Phe Arg Ser Pro His Gly
                675                 680                 685

Gln Thr Arg Pro Pro Ala Ser Leu Lys His Ile His Leu Met Pro Leu
            690                 695                 700

Ser Gln Ile Lys Lys Val Leu Asp Ile Arg Glu Thr Glu Asp Cys His
705                 710                 715                 720

Asn Ala Phe Ala Leu Leu Val Arg Pro Pro Thr Glu Gln Ala Asn Val
                725                 730                 735

Leu Leu Ser Phe Gln Met Thr Ser Asp Glu Leu Pro Lys Glu Asn Trp
            740                 745                 750

Leu Lys Met Leu Cys Arg His Val Ala Asn Thr Ile Cys Lys Ala Asp
            755                 760                 765

Ala Glu Asn Leu Ile Tyr Thr Ala Asp Pro Glu Ser Phe Glu Val Asn
            770                 775                 780

Thr Lys Asp Met Asp Ser Thr Leu Ser Arg Ala Ser Arg Ala Ile Lys
785                 790                 795                 800

Lys Thr Ser Lys Lys Val Thr Arg Ala Phe Ser Phe Ser Lys Thr Pro
                805                 810                 815

Lys Arg Ala Leu Arg Arg Ala Leu Met Thr Ser His Gly Ser Val Glu
                820                 825                 830

Gly Arg Ser Pro Ser Ser Asn Asp Lys His Val Met Ser Arg Leu Ser
            835                 840                 845

Ser Thr Ser Ser Leu Ala Gly Ile Pro Ser Pro Ser Leu Val Ser Leu
            850                 855                 860

Pro Ser Phe Phe Glu Arg Arg Ser His Thr Leu Ser Arg Ser Thr Thr
865                 870                 875                 880

His Leu Ile

<210> SEQ ID NO 3
<211> LENGTH: 2745
<212> TYPE: DNA
<213> ORGANISM: Homo sapiens
```

-continued

<400> SEQUENCE: 3

```
atggctgaaa atagtgtatt aacatccact actgggagga ctagcttggc agactcttcc        60
atttttgatt ctaaagttac tgagatttcc aaggaaaact tacttattgg atctacttca       120
tatgtagaag aagagatgcc tcagattgaa acaagagtga tattggttca agaagctgga       180
aaacaagaag aacttataaa agccttaaag actattaaaa taatggaagt ccctgttata       240
aagataaaag aaagttgtcc tggaaaatcg gatgaaaaat taataaaaag tgttattaat       300
atggacatta aagtgggctt tgtaaagatg gagtcagtgg aagaatttga aggtttggat       360
tctccggaat tgaaaatgt atttgtagtc acggactttc aggattctgt ctttaatgac        420
ctctacaagg ctgattgtag agttattgga ccaccagttg tattaaattg ttcacaaaaa       480
ggagagcctt tgccattttc atgtcgcccg ttgtattgta caagtatgat gaatctagta       540
ctatgcttta ctggatttag gaaaaaagaa gaactagtca ggttggtgac attggtccat       600
cacatgggtg gagttattcg aaaagacttt aattcaaaag ttacacattt ggtggcaaat       660
tgtacacaag gagaaaaatt cagggttgct gtgagtctag gtactccaat tatgaagcca       720
gaatggattt ataaagcttg ggaaaggcgg aatgaacagg atttctatgc agcagttgat       780
gactttagaa atgaatttaa agttcctcca tttcaagatt gtattttaag tttcctggga       840
ttttcagatg aagagaaaac caatatggaa gaaatgactg aaatgcaagg aggtaaatat       900
ttaccgcttg gagatgaaag atgcactcac cttgtagttg aagagaatat agtaaaagat       960
cttccctttg aaccttcaaa gaaactttat gttgtcaagc aagagtggtt ctggggaagc      1020
attcaaatgg atgcccgagc tggagaaact atgtatttat atgaaaaggc aaatactcct      1080
gagctcaaga atcagtgtc aatgctttct ctaaataccc ctaacagcaa tcgcaaacga       1140
cgtcgtttaa aagaaacact tgctcagctt tcaagagaga cagacgtgtc accatttcca      1200
ccccgtaagc gcccatcagc tgagcactcc ctttccatag ggtcactcct agatatctcc      1260
aacacaccag agtctagcat taactatgga gacaccccaa agtcttgtac taagtctttct     1320
aaaagctcca ctccagttcc ttcaaagcag tcagcaaggt ggcaagttgc aaaagagctt      1380
tatcaaactg aaagtaatta tgttaatata ttggcaacaa ttattcagtt atttcaagta      1440
ccattggaag aggaaggaca acgtggtgga cctatccttg caccagagga gattaagact      1500
atttttggta gcatcccaga tatctttgat gtacacacta agataaagga tgatcttgaa      1560
gaccttatag ttaattggga tgagagcaaa agcattggtg acattttttct gaaatattca     1620
aaagatttgg taaaaaccta ccctcccttt gtaaacttct ttgaaatgag caaggaaaca      1680
attattaaat gtgaaaaaca gaaaccaaga tttcatgctt ttctcaagat aaaccaagca      1740
aaaccagaat gtggacggca gagccttgtt gaacttctta ccgaccagt acagaggtta       1800
cccagtgttg cattactttt aaatgatctt aagaagcata cagctgatga aaatccagac      1860
aaaagcactt tagaaaaagc tattggatca ctgaggaag taatgacgca tattaatgag       1920
gataagagaa aaacagaagc tcaaaagcaa attttgatg ttgtttatga agtagatgga       1980
tgcccagcta atctttatc ttctcaccga agcttagtac agcgggttga acaatttct        2040
ctaggtgagc ccctgtga cagaggagaa caagtaactc tcttcctctt caatgattgc        2100
ctagagatag caagaaaacg gcacaaggtt attggcactt taggagtcc tcatggccaa       2160
acccgacccc cagcttctct taagcatatt cacctaatgc ctcttttctca gattaagaag     2220
gtattggaca taagagagac agaagattgc cataatgctt ttgccttgct tgtgaggcca     2280
```

-continued

| | | | |
|---|---|---|---|
| ccaacagagc aggcaaatgt gctactcagt ttccagatga catcagatga acttccaaaa | | | 2340 |
| gaaaactggc taaagatgct gtgtcgacat gtagctaaca ccatttgtaa agcagatgct | | | 2400 |
| gagaatctta tttatactgc tgatccagaa tcctttgaag taaatacaaa agatatggac | | | 2460 |
| agtacattga gtagagcatc aagagcaata aaaaagactt caaaaaaggt tacaagagca | | | 2520 |
| ttctctttct ccaaaactcc aaaaagagct cttcgaaggg ctcttatgac atcccacggc | | | 2580 |
| tcagtggagg gaagaagtcc ttccagcaat gataagcatg taatgagtcg tctttctagc | | | 2640 |
| acatcatcat tagcaggtat cccttctccc tcccttgtca gccttccttc cttctttgaa | | | 2700 |
| aggagaagtc atacgttaag tagatctaca actcatttga tatga | | | 2745 |

<210> SEQ ID NO 4
<211> LENGTH: 914
<212> TYPE: PRT
<213> ORGANISM: Homo sapiens

<400> SEQUENCE: 4

```
Met Ala Glu Asn Ser Val Leu Thr Ser Thr Gly Arg Thr Ser Leu
1               5                   10                  15

Ala Asp Ser Ser Ile Phe Asp Ser Lys Val Thr Glu Ile Ser Lys Glu
            20                  25                  30

Asn Leu Leu Ile Gly Ser Thr Ser Tyr Val Glu Glu Met Pro Gln
            35                  40                  45

Ile Glu Thr Arg Val Ile Leu Val Gln Glu Ala Gly Lys Gln Glu Glu
        50                  55                  60

Leu Ile Lys Ala Leu Lys Thr Ile Lys Ile Met Glu Val Pro Val Ile
65                  70                  75                  80

Lys Ile Lys Glu Ser Cys Pro Gly Lys Ser Asp Glu Lys Leu Ile Lys
                85                  90                  95

Ser Val Ile Asn Met Asp Ile Lys Val Gly Phe Val Lys Met Glu Ser
                100                 105                 110

Val Glu Glu Phe Glu Gly Leu Asp Ser Pro Glu Phe Glu Asn Val Phe
            115                 120                 125

Val Val Thr Asp Phe Gln Asp Ser Val Phe Asn Asp Leu Tyr Lys Ala
        130                 135                 140

Asp Cys Arg Val Ile Gly Pro Val Val Leu Asn Cys Ser Gln Lys
145                 150                 155                 160

Gly Glu Pro Leu Pro Phe Ser Cys Arg Pro Leu Tyr Cys Thr Ser Met
                165                 170                 175

Met Asn Leu Val Leu Cys Phe Thr Gly Phe Arg Lys Lys Glu Glu Leu
                180                 185                 190

Val Arg Leu Val Thr Leu Val His His Met Gly Gly Val Ile Arg Lys
            195                 200                 205

Asp Phe Asn Ser Lys Val Thr His Leu Val Ala Asn Cys Thr Gln Gly
        210                 215                 220

Glu Lys Phe Arg Val Ala Val Ser Leu Gly Thr Pro Ile Met Lys Pro
225                 230                 235                 240

Glu Trp Ile Tyr Lys Ala Trp Glu Arg Arg Asn Glu Gln Asp Phe Tyr
                245                 250                 255

Ala Ala Val Asp Asp Phe Arg Asn Glu Phe Lys Val Pro Pro Phe Gln
                260                 265                 270

Asp Cys Ile Leu Ser Phe Leu Gly Phe Ser Asp Glu Glu Lys Thr Asn
            275                 280                 285

Met Glu Glu Met Thr Glu Met Gln Gly Gly Lys Tyr Leu Pro Leu Gly
```

-continued

```
            290                 295                 300
Asp Glu Arg Cys Thr His Leu Val Val Glu Glu Asn Ile Val Lys Asp
305                 310                 315                 320

Leu Pro Phe Glu Pro Ser Lys Lys Leu Tyr Val Val Lys Gln Glu Trp
                325                 330                 335

Phe Trp Gly Ser Ile Gln Met Asp Ala Arg Ala Gly Glu Thr Met Tyr
                340                 345                 350

Leu Tyr Glu Lys Ala Asn Thr Pro Glu Leu Lys Lys Ser Val Ser Met
                355                 360                 365

Leu Ser Leu Asn Thr Pro Asn Ser Arg Lys Arg Arg Leu Lys
370                 375                 380

Glu Thr Leu Ala Gln Leu Ser Arg Glu Thr Asp Val Ser Pro Phe Pro
385                 390                 395                 400

Pro Arg Lys Arg Pro Ser Ala Glu His Ser Leu Ser Ile Gly Ser Leu
                405                 410                 415

Leu Asp Ile Ser Asn Thr Pro Glu Ser Ser Ile Asn Tyr Gly Asp Thr
                420                 425                 430

Pro Lys Ser Cys Thr Lys Ser Ser Lys Ser Ser Thr Pro Val Pro Ser
                435                 440                 445

Lys Gln Ser Ala Arg Trp Gln Val Ala Lys Glu Leu Tyr Gln Thr Glu
450                 455                 460

Ser Asn Tyr Val Asn Ile Leu Ala Thr Ile Ile Gln Leu Phe Gln Val
465                 470                 475                 480

Pro Leu Glu Glu Glu Gly Gln Arg Gly Gly Pro Ile Leu Ala Pro Glu
                485                 490                 495

Glu Ile Lys Thr Ile Phe Gly Ser Ile Pro Asp Ile Phe Asp Val His
                500                 505                 510

Thr Lys Ile Lys Asp Asp Leu Glu Asp Leu Ile Val Asn Trp Asp Glu
                515                 520                 525

Ser Lys Ser Ile Gly Asp Ile Phe Leu Lys Tyr Ser Lys Asp Leu Val
                530                 535                 540

Lys Thr Tyr Pro Pro Phe Val Asn Phe Phe Glu Met Ser Lys Glu Thr
545                 550                 555                 560

Ile Ile Lys Cys Glu Lys Gln Lys Pro Arg Phe His Ala Phe Leu Lys
                565                 570                 575

Ile Asn Gln Ala Lys Pro Glu Cys Gly Arg Gln Ser Leu Val Glu Leu
                580                 585                 590

Leu Ile Arg Pro Val Gln Arg Leu Pro Ser Val Ala Leu Leu Leu Asn
                595                 600                 605

Asp Leu Lys Lys His Thr Ala Asp Glu Asn Pro Asp Lys Ser Thr Leu
                610                 615                 620

Glu Lys Ala Ile Gly Ser Leu Lys Glu Val Met Thr His Ile Asn Glu
625                 630                 635                 640

Asp Lys Arg Lys Thr Glu Ala Gln Lys Gln Ile Phe Asp Val Val Tyr
                645                 650                 655

Glu Val Asp Gly Cys Pro Ala Asn Leu Leu Ser Ser His Arg Ser Leu
                660                 665                 670

Val Gln Arg Val Glu Thr Ile Ser Leu Gly Glu His Pro Cys Asp Arg
                675                 680                 685

Gly Glu Gln Val Thr Leu Phe Leu Phe Asn Asp Cys Leu Glu Ile Ala
                690                 695                 700

Arg Lys Arg His Lys Val Ile Gly Thr Phe Arg Ser Pro His Gly Gln
705                 710                 715                 720
```

```
Thr Arg Pro Pro Ala Ser Leu Lys His Ile His Leu Met Pro Leu Ser
            725                 730                 735

Gln Ile Lys Lys Val Leu Asp Ile Arg Glu Thr Glu Asp Cys His Asn
            740                 745                 750

Ala Phe Ala Leu Leu Val Arg Pro Pro Thr Glu Gln Ala Asn Val Leu
        755                 760                 765

Leu Ser Phe Gln Met Thr Ser Asp Glu Leu Pro Lys Glu Asn Trp Leu
    770                 775                 780

Lys Met Leu Cys Arg His Val Ala Asn Thr Ile Cys Lys Ala Asp Ala
785                 790                 795                 800

Glu Asn Leu Ile Tyr Thr Ala Asp Pro Glu Ser Phe Glu Val Asn Thr
            805                 810                 815

Lys Asp Met Asp Ser Thr Leu Ser Arg Ala Ser Arg Ala Ile Lys Lys
            820                 825                 830

Thr Ser Lys Lys Val Thr Arg Ala Phe Ser Phe Ser Lys Thr Pro Lys
        835                 840                 845

Arg Ala Leu Arg Arg Ala Leu Met Thr Ser His Gly Ser Val Glu Gly
850                 855                 860

Arg Ser Pro Ser Ser Asn Asp Lys His Val Met Ser Arg Leu Ser Ser
865                 870                 875                 880

Thr Ser Ser Leu Ala Gly Ile Pro Ser Pro Ser Leu Val Ser Leu Pro
            885                 890                 895

Ser Phe Phe Glu Arg Arg Ser His Thr Leu Ser Arg Ser Thr Thr His
            900                 905                 910

Leu Ile
```